United States Patent [19]
Grimm

[11] Patent Number: 5,669,890
[45] Date of Patent: Sep. 23, 1997

[54] METAL TIP ATTACHMENT FOR PLASTIC NEEDLES

[75] Inventor: C. Louis Grimm, Shawnee, Kans.

[73] Assignee: Ivy Laboratories, Inc., Overland Park, Kans.

[21] Appl. No.: 538,474

[22] Filed: Oct. 3, 1995

[51] Int. Cl.$^6$ ............................................. A61M 5/32
[52] U.S. Cl. ........................................ 604/272; 604/60
[58] Field of Search ............................ 604/60, 57, 272, 604/273, 274; 606/181, 185

[56] References Cited

U.S. PATENT DOCUMENTS

| | | |
|---|---|---|
| 2,512,569 | 6/1950 | Saffir . |
| 2,828,744 | 4/1958 | Hirsch et al. . |
| 3,347,232 | 10/1967 | Ginsburg . |
| 4,002,174 | 1/1977 | Reed et al. . |
| 4,105,030 | 8/1978 | Kercso ................................ 604/49 X |
| 4,785,868 | 11/1988 | Koenig, Jr. . |
| 4,936,827 | 6/1990 | Grimm et al. . |
| 4,946,035 | 8/1990 | Grimm et al. . |
| 5,092,848 | 3/1992 | deCiutiss . |

Primary Examiner—Mark Bockelman
Assistant Examiner—N. Kent Gring
Attorney, Agent, or Firm—Litman, McMahon and Brown, L.L.C.

[57] ABSTRACT

A metal tip attachment for a plastic needle is stamped from relatively thin sheet metal and rolled into a generally cylindrical shape adapted to conform to the outer surface of the needle. The attachment includes a pointed end and a base. Securement structure such as tabs are formed in the base and are adapted to cooperate with corresponding grooves in the outer surface of the needle for securing the attachment thereto. The attachment is secured to the needle such that at least a portion of the pointed end of the metal sheet extends slightly beyond the point of the needle.

21 Claims, 2 Drawing Sheets

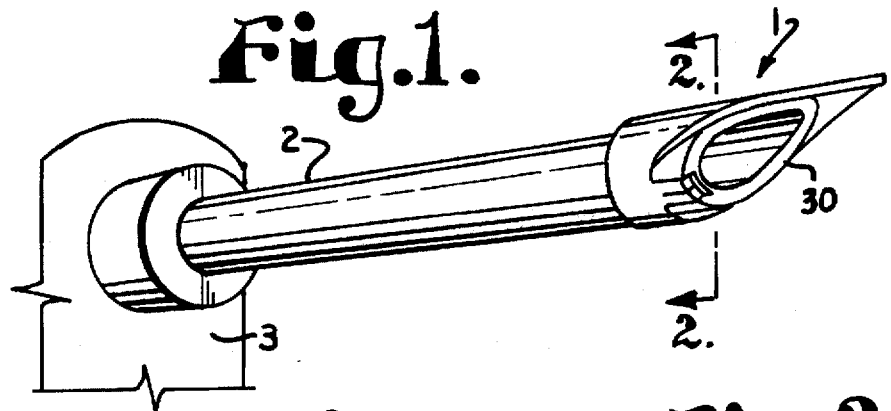
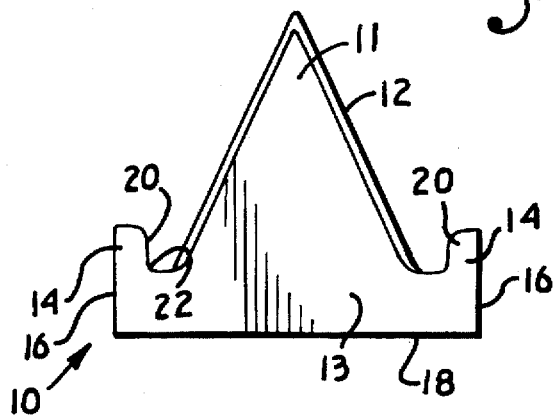
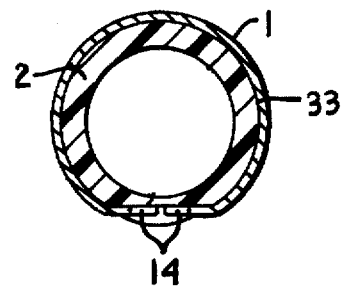
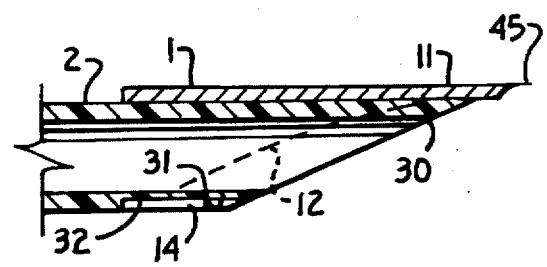
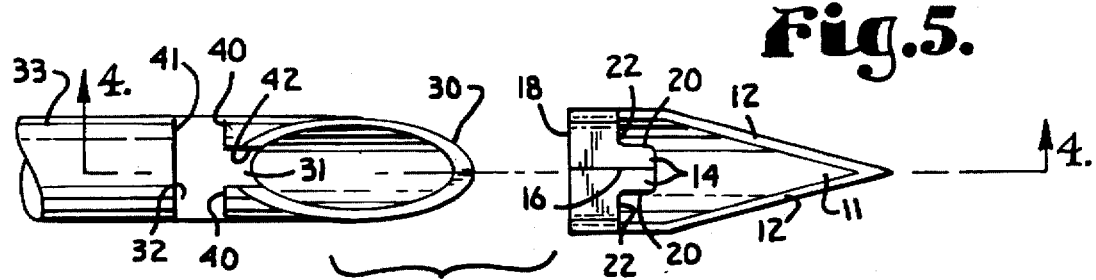

METAL TIP ATTACHMENT FOR PLASTIC NEEDLES

BACKGROUND OF THE INVENTION

I. Field of the Invention

This invention relates to a metal tip selectively attachable to a plastic needle and in particular such a metal tip adapted for attachment to plastic needles of relatively large bore such as needles used with medicament implant applicators for animals.

II. Description of the Prior Art

Implanters incorporating relatively large bore needles are widely used in livestock handling operations to insert solid or semisolid medicaments such as growth stimulating hormones into animals to be treated. Pellets containing growth stimulating hormone are typically injected into the ears of domesticated animals since the ears are commonly discarded in the slaughtering process thereby preventing unabsorbed residues from ending up in food products intended for human or domestic animal consumption.

Typical implanter devices comprise hand held instruments built of a size consistent with the size of the animal. The pellets are normally implanted while an animal is confined in a chute. An ear is grasped in one hand, and an implanter device having a large bore hypodermic needle is used to puncture the hide to enable a pellet dose to be injected between the hide and the next layer of tissue in the ear. The implanting must be done carefully to ensure that the pellets are properly placed and that no pellet remains in the puncture in the hide, which could result in an infection. At the same time, the procedure must be carried out quickly since the animals are not entirely cooperative and may shake their heads to free the held ear.

Further complicating matters is that other procedures may be occurring at the same time as the implanting operation while the animal is confined, such as ear tagging, branding, veterinary inspections or procedures, or the like, which may further excite the animal. Implanters are generally manufactured with needles made from extruded cylindrical metal which has been sheared at one end to form a point. The metal needles provide a sharp point which holds its edge through multiple implantations.

It has been a common practice to use the implanter with the same needle for multiple implantations. However, greater concerns of sanitation and cross contamination between livestock has increased the demand for implanters incorporating needles adapted for a single use or implantation. The metal needles are relatively expensive particularly when used only once. Plastic needles have been developed and generally comprise a cylindrical tube of plastic sheared at one end to form a point. The plastic needles are sufficiently sharp to pierce the ear of livestock, but require application of a slightly greater force than that necessary when using metal needles. Livestock handlers who use applicators appear to prefer metal needles over the plastic needles apparently based on the perception that the plastic needles require additional force to insert, which in turn causes the animals to be less cooperative and increases the likelihood of an improper implantation. Unfortunately, solid metal needles are relatively expensive and become somewhat cost prohibitive for use as disposable needles.

SUMMARY OF THE INVENTION

The present invention comprises a metal tip attachment for a plastic needle. The attachment is stamped or punched from relatively thin sheet metal initially in the form of a blank. The blank includes a pointed end and is rolled or otherwise shaped to conform to an outer surface of the needle. The attachment includes means for selectively securing the metal tip attachment to the needle such that the attachment extends around at least a portion of the needle and at least a portion of the pointed end of the metal sheet extends slightly beyond the point of the needle.

A pair of grooves are preferably formed in an outer surface of the needle in close proximity to the pointed end thereof. A first groove extends perpendicular to the axis of the needle lumen and the second groove extends coaxially with the axis of the needle lumen. Tabs formed on the sheet of metal are adapted to be positioned in the grooves and engaged sidewalls thereof for fixedly securing the metal tip to the end of the needle. This securement means or structure prevents the metal tip from sliding and rotating relative to the plastic needle as the plastic needle with the tip attached thereto is inserted into and removed from an animal.

OBJECTS AND ADVANTAGES OF THE INVENTION

Objects and advantages of the invention include:

providing a metal tip attachment for plastic needles;

providing such an attachment having a pointed end and adapted for securement to the needle such that at least a portion of the pointed end of the attachment extends at least slightly beyond the point of the needle;

providing such an attachment wherein the attachment is stamped from a sheet of metal and rolled to conform to the shape of a needle;

to provide such an attachment which includes a wire edge formed when the attachment is stamped from the sheet of metal;

to provide such an attachment which includes means for securing the attachment to the plastic needle such that the attachment does not slide relative to the needle during insertion and withdrawal of the needle;

to provide such an attachment which is relatively inexpensive to manufacture;

to provide such an attachment which is selectively securable to plastic needles;

to provide such an attachment which is readily securable to plastic needles and to provide such an attachment which is particularly well adapted for its intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of the metal tip attachment secured to a plastic needle of an implanter applicator.

FIG. 2 is an enlarged cross-sectional view taken along line 2—2 of FIG. 1.

FIG. 3 is an enlarged top plan view of a blank for the metal tip attachment shown in FIG. 1.

FIG. 4 is an enlarged and fragmentary cross-sectional view taken along line 4—4 of FIG. 5.

FIG. 5 is an exploded, bottom plan view of the metal tip attachment for a plastic needle as shown in FIG. 1.

DETAILED DESCRIPTION OF THE INVENTION

Figure 6:
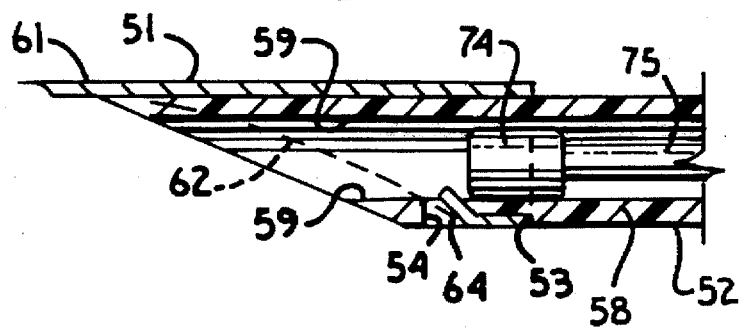
FIG. 6 is a fragmentary, cross-sectional view similar to FIG. 4 showing an alternative embodiment of the metal tip attachment.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, a metal tip attachment 1 of the present invention is shown secured to a plastic needle 2 of an implanter applicator 3 in FIG. 1. The attachment 1 is formed from a thin sheet of metal preferably stainless steel stock having a thickness of between .006 inches and .015 inches. The attachment 1 is stamped from a sheet of stock metal into the shape as shown in FIG. 3 to form a flat blank 10. The attachment 1 includes a pointed end 11 having cutting edges 12, and a base 13 having tabs 14, side edges 16 and rear edge 18. Each tab 14 includes an inner edge 20 and is spaced from a lower portion of an adjacent cutting edge 12 by forward edge 22 of the blank 10.

The attachment is adapted for use with a plastic needle 2 formed from a rigid plastic such as polycarbonate offered under the trademark Lexan by General Electric. The plastic is preferrably molded to form a cylindrical tube having an end forming a point 30. As shown in FIG. 5, first and second grooves, receptacles or recesses 31 and 32 are formed in an outer surface 33 of the needle 2 in close proximity to the point 30. The first groove 31 extends coaxially with the longitudinal axis of the needle 2. The second groove 32 extends perpendicular to the first groove 31 and transverse to the longitudinal axis of the needle 2. The first groove 31 generally opens into the second groove 32.

After the blank 10 is stamped from a sheet of stock metal, it is rolled or otherwise shaped to generally conform to the outer surface 33 of the needle 2 to which it is to be attached. In particular the sheet of metal is generally rolled into a cylindrical shape with a flattened side as shown in FIG. 2. The sheet of metal is rolled such that the side edges 16 are generally brought together in closely spaced relation and the side of the attachment including the tabs 14 is generally flattened.

The attachment 1 is attached to a needle 2 by advancing the attachment 1 across the needle point 30. The tabs 14 of the attachment 1 are biased outward as the rear edge 18 of the attachment 1 is advanced past the rearmost portion of the needle point 30. As the tabs 14 and rear portion of the attachment 1 are advanced into alignment with the grooves 31 and 32, the tabs 14 and the rear portion of the attachment 1 are biased into the grooves 31 and 32 respectively. The portion of the attachment 1 biased into the grooves 31 and 32 may generally be referred to as securement structure and comprise the preferred means for securing the attachment 1 to the needle 2.

The forward edges 22 of the attachment 1 abut against a forward wall 40, defining groove 31, and the rear edge 18 abuts against a rear wall 41, defining groove 31, when the rear portion of the attachment is biased into the groove 31 preventing the attachment 1 from advancing rearward or forward along the length of the needle 2. The inner edge 20 of each tab 14 engages a respective outer wall 42, defining groove 32, when the tabs 14 are biased into the groove 32 preventing the tabs 14 from separating and preventing the attachment 1 from rotating relative to the needle 2.

When the attachment 1 is secured to the needle 2, a portion of the pointed end 11 of the attachment 1, and therefore a portion of the cutting edges 12, extend slightly beyond the needle point 30. The pointed end 11 shown in the blank 10 is triangular.

The metal stamping process used to form blank 10 may create what is referred to as a wire edge or burr 45 extending around the outer edge of the blank 10. The wire edge is extremely sharp. Such burrs are typically sanded off or otherwise removed from stamped metal to prevent unwanted cuts during handling. However, in the present application, the wire edge 45 may be left on the blank, at least along the cutting edge 12 thereof, to provide an even sharper edge to facilitate penetration. The blank 10 is preferably rolled such that the wire edge 45 forms an extension of the outer surface of the attachment 1.

An alternative embodiment of the attachment 51 for a needle 52 is shown in FIG. 6. The needle 52 includes a first groove 53 extending coaxially with the longitudinal axis of the needle 52 and a second groove 54 extending perpendicular to the longitudinal axis of the needle 52. The first groove 53 extends completely through the wall 58 of the needle 52 and opens into the needle lumen 59. The attachment includes a pointed end 61, cutting edges 62 and tabs 64. The tabs 64 are bent such that when the attachment 51 is secured to the needle 52, the tabs 64 extend partially into the lumen 59. The tabs 64 may be biased out of the lumen 59 by application of a force thereto. The tabs 64 extending into the lumen 59, act as a stop to prevent medicament pellets 74 from sliding out of the lumen 59 except upon application of a force such as may be applied by impeller rod 75 used to drive the pellet 74 past the tabs 64, out of the needle 52 and into the recipient.

Figure 7:
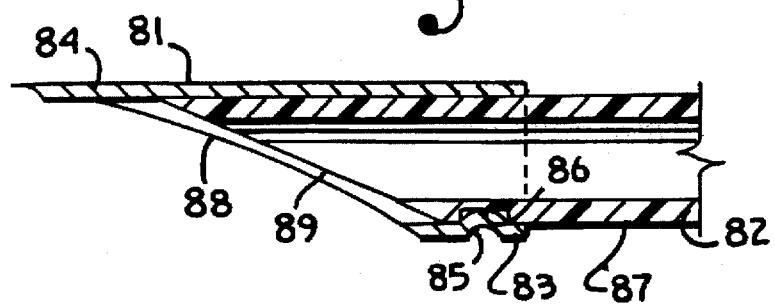
FIG. 7 is a fragmentary, cross-sectional view similar to FIG. 4 showing an alternative embodiment of the metal tip attachment secured to a plastic needle.
Figure 8:
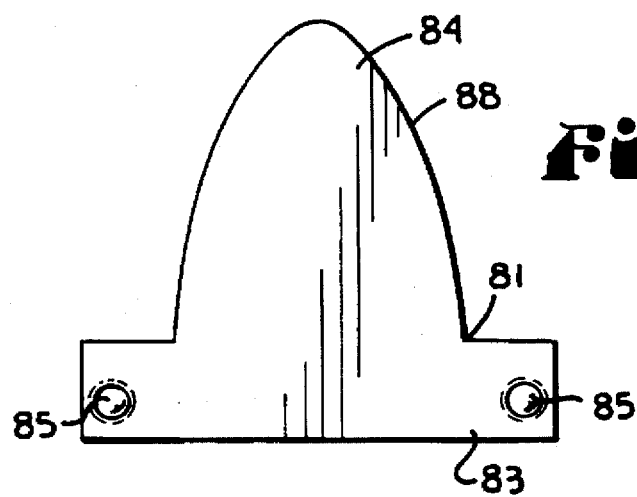
FIG. 8 is a top plan view of a blank for the alternative embodiment of the metal tip attachment of the present invention as shown in FIG. 7.

FIGS. 7 and 8 show another embodiment of the present invention incorporating alternative means for securing an attachment 81 to a needle 82. The attachment 81 includes a base 83 and a pointed end 84. Bosses or projections 85 are formed in the base 83 and extend radially inward from the attachment 1 in the cylindrical configuration. The bosses 85 are adapted to engage corresponding grooves, recesses or indentations 86 formed in an outer surface 87 of the needle 82 for securing the attachment 81 to the needle 82 and preventing further linear or rotational advancement of the attachment 81 with respect to the needle 82. It is foreseen that the bosses 85 and indentations 86 may be of varying number and shapes.

The shape of the pointed end 84 is generally ovate to increase the portion of cutting edges 88 which extend beyond the edge of needle point 89. It is foreseen that the shape of the pointed end may be further varied to vary the portion of the cutting edges 88 which extend beyond the needle point 89.

It is to be understood that while certain forms of the present invention have been illustrated and described herein, it is not to be limited to the specific forms or arrangement of parts described and shown.

What is claimed and desired to be secured by Letters Patent is as follows:

1. A plastic needle in combination with a metal tip attachment wherein said needle includes an outer surface and a point at one end thereof; said attachment comprising a metal sheet having a pointed end and shaped to conform to the outer surface of said needle; said combination further including mating structure on said plastic needle and said attachment cooperating to allow said attachment to be selectively secured to said needle such that a user can utilize said needle with or without said attachment and such that said metal sheet extends around at least a portion of said needle and at least a portion of said pointed end of said metal sheet extends at least slightly beyond said point of said needle when said attachment is secured to said needle.

2. The attachment of claim 1 wherein said metal sheet includes a wire edge extending along at least a portion of a pointed end of said metal sheet.

3. The attachment of claim 1 wherein said pointed end is triangular.

4. The attachment of claim 1 wherein said pointed end is ovate.

5. A plastic needle in combination with a metal tip attachment wherein:
   a. a first groove is formed in an outer surface of said needle proximate a point at one end of said needle;
   b. said attachment is formed from a metal sheet having a pointed end; said metal sheet being shaped to conform to said outer surface of said needle; said attachment including securement structure extending into said groove on said needle when said attachment is positioned on said needle proximate said needle point so as to engage said needle and secure said attachment thereto to allow said attachment to be selectively secured to said needle such that a user can utilize said needle with or without said attachment and such that at least a portion of said pointed end of said metal sheet extends at least slightly beyond said point of said needle.

6. The combination of claim 5 wherein said first groove extends through a needle wall and into a needle lumen extending through said needle; a portion of said securement structure extending through said first groove and into said needle lumen when said attachment is secured to said needle; said securement structure biasable out of said needle lumen upon application of a force on said structure from within said needle lumen.

7. The attachment of claim 5 wherein said metal sheet includes a wire edge extending along at least a portion of a pointed end of said metal sheet.

8. The attachment of claim 5 wherein said pointed end is triangular.

9. The attachment of claim 5 wherein said pointed end is ovate.

10. A plastic needle in combination with a metal tip attachment wherein:
    a. a first groove is formed in an outer surface of said needle proximate a point of said needle; said first groove extends coaxially with the longitudinal axis of said needle a second groove is formed in said outer surface of said needle and extends perpendicular to said first groove;
    b. said attachment is formed from a metal sheet having a pointed end; said metal sheet is shaped to conform to said outer surface of said needle; said attachment including structure extending into said first and second grooves on said needle when said needle is positioned on said needle proximate said needle point such that at least a portion of said pointed end of said metal sheet extends at least slightly beyond said point of said needle.

11. The combination of claim 10 wherein said first groove extends through a needle wall and into a needle lumen extending through said needle; a portion of said securement structure extending through said first groove and into said needle lumen when said attachment is secured to said needle; said securement structure biasable out of said needle lumen upon application of a force on said structure from within said needle lumen.

12. The attachment of claim 10 wherein said metal sheet includes a wire edge extending along at least a portion of said pointed end of said metal sheet.

13. The attachment of claim 10 wherein said pointed end is triangular.

14. The attachment of claim 10 wherein said pointed end is ovate.

15. A method for forming a metal attachment tip for plastic needles comprising the steps of:
    a. forming from a relatively thin sheet of metal a flat blank having a pointed end and a base incorporating securement structure therein;
    b. shaping the blank into a generally cylindrical shape conforming to the shape of said needle; said securement structure positioned to cooperatively engage a receptacle on said needle to allow said attachment to be selectively secured to said needle such that a user can utilize said needle with or without said attachment; said attachment shaped such that said base at least partially circumscribes said needle when secured to said needle and at least a portion of said pointed end extends beyond a point of said needle.

16. The method of claim 15 wherein said blank is formed from said sheet metal by a stamping process and said stamping process leaves a wire edge extending at least partially around said pointed end.

17. The method of claim 15 wherein said blank is formed such that said pointed end is triangular.

18. The method of claim 15 wherein said blank is formed such that said pointed end is ovate.

19. The method of claim 15 wherein said blank is formed such that said securement structure comprises at least one tab extending from said base and said blank is shaped into a generally cylindrical shape with the side of said attachment including said tab being flattened such that said tab is adapted to be positioned in a receptacle on said needle for selectively securing said attachment thereto.

20. A plastic needle in combination with a metal tip attachment wherein:
    a. a first groove is formed in an outer surface of said needle proximate a point at one end of said needle;
    b. said attachment is formed from a metal sheet having a pointed end; said metal sheet being shaped to conform to said outer surface of said needle; said attachment including securement structure extending into said groove on said needle when said attachment is positioned on said needle proximate said needle point such that at least a portion of said pointed end of said metal sheet extends at least slightly beyond said point of said needle;
    c. said first groove extends through said needle wall into a needle lumen extending through said needle; and d. said securement structure extends into said needle lumen when said attachment is secured to said needle; said securement structure biasable out of said needle lumen upon application of a force on said structure from within said needle lumen.

21. A method for forming a metal attachment tip for plastic needles comprising the steps of:

a. forming from a relatively thin sheet of metal a flat blank having a pointed end and a base incorporating securement structure therein;

b. shaping the blank into a generally cylindrical shape conforming to the shape of said needle; said securement structure positioned to cooperatively engage a receptacle on said needle for securing said attachment to said needle; said attachment shaped such that said base at least partially circumscribes said needle when secured to said needle and at least a portion of said pointed end extends beyond a point of said needle; and c. said blank is formed from said sheet metal by a stamping process and said stamping process leaves a wire edge extending at least partially around said pointed end.

* * * * *